United States Patent
Kaiser et al.

(10) Patent No.: US 10,213,623 B2
(45) Date of Patent: Feb. 26, 2019

(54) MONITORING A PATIENT'S POSITION USING A PLANNING IMAGE AND SUBSEQUENT THERMAL IMAGING

(71) Applicant: Brainlab AG, Munich (DE)

(72) Inventors: Hagen Kaiser, Icking (DE); Ivana Ivanovska, Aschheim (DE)

(73) Assignee: Brainlab AG, Munich (DE)

( * ) Notice: Subject to any disclaimer, the term of this patent is extended or adjusted under 35 U.S.C. 154(b) by 0 days.

(21) Appl. No.: 15/741,968

(22) PCT Filed: May 3, 2017

(86) PCT No.: PCT/EP2017/060567
§ 371 (c)(1),
(2) Date: Jan. 4, 2018

(87) PCT Pub. No.: WO2017/191207
PCT Pub. Date: Nov. 9, 2017

(65) Prior Publication Data
US 2018/0193667 A1    Jul. 12, 2018

Related U.S. Application Data

(63) Continuation-in-part of application No. PCT/EP2016/060032, filed on May 4, 2016.

(51) Int. Cl.
*G06F 19/00* (2018.01)
*A61N 5/10* (2006.01)
(Continued)

(52) U.S. Cl.
CPC .......... *A61N 5/1049* (2013.01); *A61B 5/0035* (2013.01); *A61B 5/015* (2013.01);
(Continued)

(58) Field of Classification Search
CPC .......... A61N 5/1049; A61N 2005/1054; A61N 5/1069; A61B 5/015; A61B 6/0492;
(Continued)

(56) References Cited

U.S. PATENT DOCUMENTS 6,405,072 B1    6/2002   Cosman
7,016,522 B2    3/2006   Bani-Hasemi
(Continued)

FOREIGN PATENT DOCUMENTS

FR         2946243 A1    12/2010
WO    WO 2001/059708 A1   8/2001

OTHER PUBLICATIONS

"Marching Cubes: A High Resolution 3D Surface Construction Algorithm" Based on the Paper by William E. Lornsen and Harvey E Cline. Retrieved Feb. 17, 2016.
(Continued)

*Primary Examiner* — Courtney D Thomas
(74) *Attorney, Agent, or Firm* — Middleton Reutlinger (57) ABSTRACT

Disclosed is a computer-implemented medical data processing method for supporting positioning a patient for treatment by at least one of radiotherapy or radiosurgery, the method comprising executing, on at least one processor of at least one computer, steps of: a) acquiring (S11), at the at least one processor, planning image data describing a digital planning image of an anatomical body part of a body (1) of the patient; b) acquiring (S12), at the at least one processor, planning image alignment data describing a relative position between the anatomical body part and a predetermined reference position at the point in time when the planning image data was generated; c) acquiring (S13), at the at least one processor, thermal reference image data describing a thermal reference image of the anatomical body part; d) acquiring (S14), at the at least one processor, thermal
(Continued)

imaging device reference position data describing a relative position between a thermal imaging device (17) used for taking the thermal reference image and the predetermined reference position; e) determining (S15), by the at least one processor and based on the planning image data and the planning image alignment data and the thermal image data and the thermal imaging device position data, image projection data describing a projection of the image representation of at least the anatomical body part described by the planning image data onto the image representation of the anatomical body part described by the thermal reference image data.

15 Claims, 5 Drawing Sheets

(51) Int. Cl.

| | | |
|---|---|---|
| A61B 6/04 | (2006.01) | |
| A61B 6/00 | (2006.01) | |
| A61B 5/01 | (2006.01) | |
| A61B 5/00 | (2006.01) | |
| A61B 6/03 | (2006.01) | |
| A61B 5/11 | (2006.01) | |

(52) U.S. Cl.
CPC .......... *A61B 6/0492* (2013.01); *A61B 6/5247* (2013.01); *G06F 19/00* (2013.01); *A61B 5/1114* (2013.01); *A61B 6/032* (2013.01); *A61B 6/5229* (2013.01); *A61B 2505/05* (2013.01); *A61B 2560/0223* (2013.01); *A61B 2576/00* (2013.01); *A61B 2576/02* (2013.01); *A61N 5/1069* (2013.01); *A61N 2005/1054* (2013.01); *A61N 2005/1059* (2013.01)

(58) Field of Classification Search
CPC ... A61B 5/0035; A61B 6/5229; A61B 5/1114; A61B 2576/02; A61B 6/5247; A61B 6/032; A61B 2505/05; A61B 2576/00; G06F 19/00
See application file for complete search history.

(56) References Cited

U.S. PATENT DOCUMENTS

| | | | |
|---|---|---|---|
| 2007/0003123 A1* | 1/2007 | Fu | ........................ A61N 5/1049 382/131 |
| 2013/0235163 A1 | 9/2013 | Joo | |
| 2014/0037173 A1 | 2/2014 | Gum et al. | |
| 2015/0272530 A1* | 10/2015 | Umekawa | .............. A61B 6/035 378/7 |

OTHER PUBLICATIONS

International Search Report and Written Opinion, European Patent Office for PCT/2017/060567 dated Jul. 5, 2017.
Zhang, Zhengyou "A Flexible new Technique for Camera Calibration", IEEE Transactions on Pattern Analysis and Machine Intelligence, 22(11): 1330-1334. 2000.
Crivellaro, et al. "Dense Methods for Image Alignment with an Application to 3D Tracking" EPFL Report 197866. Mar. 25, 2014.
Lucas, et al. "An Iterative Image Registration Technique with an Application to Stereo Vision" Proceedings of Imaging Understanding Workshop, pp. 121-130. 1981.
Kneip, et al. "A Novel Parametrization of the Perspective-Three-Point Problem for a Direct Computation of Absolute Camera Position and Orientation" IEEE Conference on Computer Vision and Pattern Recognition. 2011.

* cited by examiner

Fig. 5 ated computer program, a non-transitory program storage
MONITORING A PATIENT'S POSITION USING A PLANNING IMAGE AND SUBSEQUENT THERMAL IMAGING The present invention relates to a computer-implemented method for supporting positioning a patient for treatment by at least one of radiotherapy or radiosurgery, a corresponding computer program, a non-transitory program storage medium storing such a program and a computer for executing the program, as well as a system for supporting positioning a patient for treatment by at least one of radiotherapy or radiosurgery, the system comprising an electronic data storage device and the aforementioned computer.

TECHNICAL BACKGROUND

In radiotherapy and radiosurgery it is of great importance to have reliable information about the correct placement of the patient (specifically, the target to be irradiated with a treatment beam) relative to the beam source. For example, the patient needs to be correctly pre-positioned on the treatment couch so that any finer positioning algorithm will have a good start point for successful execution of the positioning algorithm. Previous approaches to pre-positioning include determination of the patient's position by detecting reflecting markers fixedly attached to the patient's body in a known spatial relationship. Such, however, requires the markers to be kept clean during the positioning procedure and requires a further step to the pre-positioning procedure which involves attaching the markers.

In general, the registration between a video image and a CT dataset is usable for patient motion management in the framework of radiotherapy or radiosurgery and (if accurate enough) also for patient positioning as the video image (such as an infrared video image) is free of ionizing radiation and available in high frame rates. Thus the patient's position can be verified several times per second.

The following two prior art approaches for monitoring the patient's position on the basis of infrared videos are known:
1. Real-time patient monitoring is currently done by fusing point clouds from a range camera with a reference point cloud that either comes from an aligned CT or a range camera's point cloud taken at reference position. Registration between point clouds is instable and computationally demanding. Current Range Cameras are either slow and/or not accurate. Point clouds are often incomplete and noisy which complicates the registration process even more. Range Cameras are expensive, and subject to the surface quality of the object of interest.
2. The prior art tries to register two modalities (CT with video) directly. To achieve the minimization they must find a way for one modality to mimic the other modality. In X-Ray/CT Registration e.g. DRRs (digitally rendered radiographs) are a way for the CT modality to 'mimic' an X-Ray. Then the registration tries to find the DRR which is most 'similar' to the CT. The prior art tries to do the same thing by generating virtual video images from the CT and assumptions about the treatment room lighting and general skin colour, and assuming to know that the patient is naked. All these assumptions are of course inaccurate and error-prone. Even under very good conditions it is doubtful that this virtual image is able to 'mimic' the real video image in any way.

The inventors acknowledge the fact that a CT and a thermal image cannot be registered directly as there is no good similarity measure known. It however is possible to register CBCT (cone-beam computed x-ray tomography) or stereo x-ray to the machine isocentre. Using these techniques, a CT can be aligned to the current patient position in an isocentric coordinate system (i.e. a coordinate system which rest relative to/and or in the isocentre). Furthermore, it is possible to register a thermal camera to the isocentric coordinate system using a suitable calibration phantom and a calibration procedure known form the state of the art. So once a CT has been aligned to the live (current) position of the patient in the treatment-room, the CT is aligned in the same coordinate system as the video/thermal camera. Being able to calculate now the position of the camera relative to the CT we can project the CT surface into the camera's image.

Thus we receive a reference set of coloured 2D/3D points of the patient's surface which can serve as the basis for the application of any RGB-D or pure visual registration algorithm (which both may be known from the state of the art) for registering a current image against the reference set and realize patient motion management.

The present invention is designed to achieve patient motion management for pre-positioning or monitoring the patient's position on the basis of a planning CT and infrared images taken after placing the patient ready for therapy.

The present invention can be used in connection with a system for image-guided radiotherapy such as ExacTrac®, a product of Brainlab AG.

Aspects of the present invention, examples and exemplary steps and their embodiments are disclosed in the following. Different exemplary features of the invention can be combined in accordance with the invention wherever technically expedient and feasible.

EXEMPLARY SHORT DESCRIPTION OF THE PRESENT INVENTION

In the following, a short description of the specific features of the present invention is given which shall not be understood to limit the invention only to the features or a combination of the features described in this section.

The disclosed method encompasses monitoring a patient's position relative to the isocentre of a radiotherapy/radiosurgery treatment device by registering a thermal reference image to a planning image (such as a planning CT) to check the correct initial positioning of the patient relative to the beam source, and then taking subsequent thermal current images showing the patient's position over time. The position extracted from the thermal current images is then compared to the position extracted from the thermal reference image to determine whether the patient has moved. If this is the case, at least one of the position of the couch on which the patient is placed, the position of the beam source or the predetermined treatment plan may be changed so as to be suitably adapted to the current position of the patient so as to carry out the envisaged medical procedure.

GENERAL DESCRIPTION OF THE PRESENT INVENTION

In this section, a description of the general features of the present invention is given for example by referring to possible embodiments of the invention.

In general, the invention reaches the aforementioned object by providing, in a first aspect, a computer-implemented method for supporting positioning (for example, pre-positioning or monitoring the position of) a patient for treatment by at least one of radiotherapy or radiosurgery. The method comprises executing, on at least one processor of at least one computer, the following exemplary steps which are executed by the at least one processor.

In a (for example first) exemplary step, planning image data is acquired which describes (for example, defines or represents) a digital planning image of an anatomical body part of a body of the patient. The planning image data has been generated with at least one of different medical imaging modalities such as computed x-ray tomography (CT), magnetic resonance tomography (MRT), ultrasound tomography or thermal (infrared) imaging. Hence, the planning image data is defined in at least three-dimensional coordinates. For example, the planning image data has been generated by applying a tomographic imaging modality (e.g. CT, MRT or ultrasound) to the anatomical body part, or by imaging the anatomical body part with an infrared-sensitive imaging device. The step of generating the planning image data is not necessarily part of the disclosed method, but may under circumstances be part of the disclosed method. In one example, the planning image data has been generated before execution of the disclosed method starts so that the planning image data is predetermined and merely used as an input to the disclosed method. For example, the planning image is taken before the patient is placed ready (pre-positioned) for the at least one of radiotherapy or radiosurgery. The anatomical body part can generally be any body part but in examples may comprise (specifically, be) the patient's head or torso.

In a further (for example second) exemplary step, planning image alignment data is acquired which describes (for example, defines or represents) a relative position between the anatomical body part and a predetermined reference position at the point in time when the planning image data was generated. The relative position is for example predetermined, i.e. known before the execution of the disclosed method starts, and the planning image alignment data is for example generated before the execution of the disclosed method starts and then used as an input to the disclosed method. Alternatively, the planning alignment image data is generated and the relative position is computed while the disclosed method is being executed. The relative position can be computed by applying for example the algorithm described in Kneip, L., Scaramuzza, D., Siegwart, R.: A Novel Parametrization of the Perspective-three-Point Problem for a Direct Computation of Absolute Camera Position and Orientation. In: Proc. of CVPR 2011, pp. 2969-2976 (2011) in combination with marker-based tracking and a corresponding marker-augmented phantom. In general terms, this involves determining (e.g. by applying considerations from basic linear algebra) a transformation (i.e. a linear mapping) between a coordinate system used for positioning the patient (which may be centred in the reference position) and the coordinate system in which the digital planning image was generated (which may be fixed with regard to the imaging device used for generating the planning image data), for example, based on knowledge of the relative position between the imaging device used for generating the planning image data and the reference position. In one example, the predetermined reference position is the isocentre of a treatment device usable for treating the patient with at least one of radiotherapy or radiosurgery. The isocentre according to a definition established in the art is the point in space relative to the treatment device about which various components of the linac (linear accelerator used to generate treatment radiation) rotate. The gantry rotation defines a horizontal axis which intersects a vertical axis defined by the rotation of the treatment couch. The treatment collimators also rotate about an axis pointing through the isocentre. The information defining the relative position is defined in for example three-dimensional coordinates and can be represented by for example a matrix (in a specific case, by a vector).

In a further (for example third) exemplary step, thermal reference image data is acquired which describes (for example, defines or represents) a thermal reference image of the anatomical body part. The thermal reference image is an infrared image generated by imaging the anatomical body part using a thermal imaging device (i.e. an infrared-sensitive imaging device) such as an infrared camera (for example, an infrared-sensitive stereo-camera). This process is also called thermography of the anatomical body part. The thermal reference image is for example a digital image (for example, a video image or a still image). The thermal reference image data in one example is defined in two-dimensional coordinates. The thermal reference image is taken in one example after the patient has been placed ready for the envisaged treatment by radiotherapy or radiosurgery.

In a further (for example fourth) exemplary step, thermal imaging device reference position data is acquired which describes (for example, defines or represents) a relative position between the thermal imaging device used for taking the thermal reference image and the predetermined reference position. The relative position is for example predetermined, i.e. known before the execution of the disclosed method starts, and the thermal imaging device reference position data is generated for example before the execution of the disclosed method starts and then used as an input to the disclosed method. Alternatively, the thermal imaging device reference position data is generated and the relative position is computed while the disclosed method is being executed. The relative position can be computed by applying for example the algorithm described Kneip, L., Scaramuzza, D., Siegwart, R.: A Novel Parametrization of the Perspective-three-Point Problem for a Direct Computation of Absolute Camera Position and Orientation. In: Proc. of CVPR 2011, pp. 2969-2976 (2011) in combination with a marker-based tracking and a corresponding phantom augmented with thermal active markers. To calibrate the camera for lens-distortion effects Zhang, Z.: "A flexible new technique for camera calibration." Pattern Analysis and Machine Intelligence, IEEE Transactions on 22.11 (2000): pp. 1330-1334 can be used using for example a similar phantom. In a further example, the relative position is fixed, i.e. does not change in space over time. The information defining the relative position is defined in for example three-dimensional coordinates and can be represented by for example a matrix (in a specific case, by a vector).

In a further (for example fifth) exemplary step, image projection data is determined which describes (for example, defines or represents) a projection of the image representation of at least the anatomical body part described by the planning image data onto the image representation of the anatomical body part described by the thermal reference image data. The image projection data is determined based on (for example, from) the planning image data and the planning image alignment data and the thermal image data and the thermal imaging device position data. After the registration result (the relative position described by the planning image alignment data) calculated in the above-described exemplary second step is known, a thermal image (an infrared image) of the anatomical body part is taken. Using the camera model (the relative position described by the thermal imaging device reference position data in combination with the lens distortion parameters), we acquire a set of corresponding 2D/3D points corresponding to each other in the thermal reference image and in the digital planning image by applying a mapping which is based on the relative position between the thermal imaging device used for taking the thermal reference image and the predetermined reference position to all (visible) surface points of the digital planning image. A correspondence is received for each pixel in the thermal reference image for which a corresponding point on the 3D surface described by the digital planning image exists. To extract the surface points of a tomography, e.g. a CT, for example a "Marching Cubes" algorithm can be used like described in Lorensen, W. E. and Cline, H. E.: Marching Cubes: A high resolution 3D surface construction algorithm. In: Computer Graphics, vol. 21, no. 4, July 1987, pp. 163-169.

In an example of this exemplary fifth step, body part reference position data is determined which describes (for example, defines or represents) a relative position between the anatomical body part and the reference position at the point in time at which the thermal reference image was taken. The body part reference position data is determined based on (for example, from) the thermal reference image data and the thermal imaging device reference position data. Specifically, the relative position between the anatomical body part and the reference position at the point in time at which the thermal reference image was taken is computed by transforming the relative position between the anatomical body part and the thermal imaging device into the coordinate system in which the reference position is defined (for example, in which the reference position rests), which may be the isocentric coordinate system. This transformation is performed using the knowledge about the relative position described by the thermal imaging device reference position data. The image projection data may then be determined based on the body part reference position data.

In a further example, the disclosed method comprises steps of acquiring thermal current image data which describes (for example, defines or represents) a thermal current image of the anatomical body part which has been taken after the thermal reference image was taken; and determining, based on (for example, from) the thermal current image data and the thermal reference image data, thermal position history data which describes (for example, defines or represents) a positional history of the anatomical body part described by a transformation between the position of the anatomical body part at the point in time at which the thermal reference image was taken and the position of the anatomical body at the point in time at which the thermal current image was taken.

The thermal current image is for example a digital image (for example, a video image or a still image). Generating the positional history resembles a positional tracking (i.e. spatial tracking over time) of the anatomical body part relative to e.g. its position described by the body part reference position data.

In this example, the method may further comprise optional steps of:

acquiring thermal imaging device current position data which describes (for example, defines or represents) a relative position between a thermal imaging device used for taking the thermal current image and the predetermined reference position (in a specific case, the thermal imaging device used for taking the thermal current image is identical to the thermal imaging device used for taking the thermal reference image); and determining based on (for example, from) the thermal current image data and the thermal imaging device current position data, body part current position data describing a relative position between the anatomical body part and the reference position at the point in time at which the thermal current image was taken.

The thermal position history data may then be determined based on (for example, from) the body part current position data by including the relative position described by the body part current position data in a time series of positions of the anatomical body part (for example in the coordinate system in which the reference position rests), or by comparing the relative position described by the body part current position data to the previous position of the anatomical body part in order to determine whether there has been a change in position (i.e. a movement of the anatomical body part relative to for example its previous position or relative to the reference position). The relative position described by the thermal imaging device current position data may be determined in analogy to the above-described way of determining the relative position described by the thermal imaging device reference position data. The relative position described by body part current position data may be determined in analogy to the above-described way of determining relative position described by the body part reference position data. This may also be done in case the positional calibration of the thermal imaging device has been updated (i.e. if the relative position described by the thermal imaging device current position data has been changed) while the disclosed method is being executed, for example because the camera moved relative to the reference position. If the thermal imaging device used for taking the thermal current image is identical to the thermal imaging device used for taking the thermal reference image and as long as such an update has not occurred, the thermal imaging device current position data is identical to the thermal imaging device reference position data because the positional calibration of the thermal imaging device does not change.

In this example, the disclosed method may comprise an optional step of determining, based on (for example, from) the thermal reference image data and the thermal current image data, thermal transformation data describing a transformation between the reference thermal image and the current thermal image. The thermal position history data may then be determined based on (for example, from) the thermal transformation data. The transformation is a spatial mapping represented for example by a linear mapping function. The transformation may be determined for example by pixel-wise comparison of the thermal reference image to the thermal current image. Alternatively or additionally, the transformation may be determined by applying an image fusion algorithm to the thermal reference image and the thermal current image in order to determine a mapping between corresponding image features in both images, or by segmenting image features such as contours, corners or blobs in both images and comparing the positions of the respective image features to one another.

In this example, the disclosed method may comprise an optional step of determining, based on (for example, from) the thermal position history data, positional difference data which describes (for example, defines or represents) a difference between the position of the anatomical body part at the point in time at which the thermal reference image was taken and the position of the anatomical body at the point in time at which the thermal current image was taken. For example, the positional difference data describes a possibly multi-dimensional (for example, three-dimensional) value of the aforementioned difference. The difference can be determined for example by subtraction of the relative position between the position of the anatomical body part at the point in time at which the thermal reference image was taken from the position of the anatomical body at the point in time at which the thermal current image was taken (or vice versa). A difference unequal to zero indicates a change in the position, i.e. a movement of the anatomical body part.

Within this optional step, the disclosed method may comprise optional steps of
- acquiring positional difference threshold data which describes (for example, defines or represents) a (possible multi-dimensional, for example three-dimensional) threshold value of the difference between the position of the anatomical body part at the point in time at which the thermal reference image was taken and the position of the anatomical body at the point in time at which the thermal current image was taken; and
- determining, based on (for example, from) the positional difference data and the positional difference threshold data, treatment control data which describes (for example, defines or represents) a command for controlling a treatment device usable for the at least one of radiotherapy or radiosurgery. The command may be embodied by digital information or an electronic signal.

In one exemplary embodiment of those optional steps, the treatment control data is determined by comparing the difference between the position of the anatomical body part at the point in time at which the thermal reference image was taken and the position of the anatomical body at the point in time at which the thermal current image was taken on the one hand to the threshold value on the other hand, for example by establishing a difference between the value of the difference and the threshold value. For example, the control data is determined if (for example, only if) the comparison results in that the difference exceeds the threshold value.

The command for controlling the treatment device in one example of the above optional steps comprises at least one of
- a command for controlling emission of a treatment beam by a beam source of the treatment device; or
- a command for changing a relative position between the patient's body and the beam source, for example by moving a patient support unit of the treatment device (onto which the patient has been placed, for example onto which he has been fixated).
- Alternatively od additionally, the command may comprise information for adapting a treatment plan (i.e. the planned beam manifold) to the current position of the patient.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the second aspect is stored.

In a fourth aspect, the invention is directed to at least one computer (for example, a computer), comprising at least one processor (for example, a processor) and at least one memory (for example, a memory), wherein the program according to the second aspect is running on the processor or is loaded into the memory, or wherein the at least one computer comprises the program storage medium according to the third aspect.

In a fifth aspect, the invention is directed to a system for supporting positioning a patient for treatment by at least one of radiotherapy or radiosurgery, the system comprising:
a) the at least one computer according to the fourth aspect;
b) at least one electronic data storage device storing at least the planning image data, the planning image alignment data and thermal imaging device reference position data;
c) a thermal imaging device for taking the reference thermal image, the thermal imaging device being operably coupled to the at least one computer for transmitting a signal to the at least one computer corresponding to the thermal reference image data;
d) a treatment device usable for treating the patient with at least one of radiotherapy or radiosurgery; and
e) a patient support unit for supporting the patient's body.

The at least one computer is operably coupled to the at least one electronic data storage device for acquiring, from the at least one data storage device, the planning image data, the planning image alignment data and thermal imaging device reference position data. Furthermore, the computer is operably coupled to at least one of the treatment device or the patient support unit. The treatment device is operably coupled to, for example comprises, at least one beam source for generating treatment radiation (ionizing radiation), for example a high-energy x-ray tube or a linear accelerator.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of radiotherapy or radiosurgery. More particularly, the invention does not involve or in particular comprise or encompass any surgical or therapeutic activity. The invention is instead directed as applicable to positioning a patient relative to the treatment device for example before any radiotherapy or radiosurgery ensues. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

The present invention relates to the field of controlling a treatment beam. The treatment beam treats body parts which are to be treated and which are referred to in the following as "treatment body parts". These body parts are for example parts of a patient's body, i.e. anatomical body parts.

The present invention relates to the field of medicine and for example to the use of beams, such as radiation beams, to treat parts of a patient's body, which are therefore also referred to as treatment beams. A treatment beam treats body parts which are to be treated and which are referred to in the following as "treatment body parts". These body parts are for example parts of a patient's body, i.e. anatomical body parts. Ionising radiation is for example used for the purpose of treatment. For example, the treatment beam comprises or consists of ionising radiation. The ionising radiation comprises or consists of particles (for example, sub-atomic particles or ions) or electromagnetic waves which are energetic enough to detach electrons from atoms or molecules and so ionise them. Examples of such ionising radiation include x-rays, high-energy particles (high-energy particle beams) and/or ionising radiation emitted from a radioactive element. The treatment radiation, for example the treatment beam, is for example used in radiation therapy or radiotherapy, such as in the field of oncology. For treating cancer in particular, parts of the body comprising a pathological structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

DESCRIPTION OF THE FIGURES

In the following, the invention is described with reference to the appended figures which represent a specific embodiment of the invention. The scope of the invention is however not limited to the specific features disclosed in the context of the figures, wherein.

Figure 1:
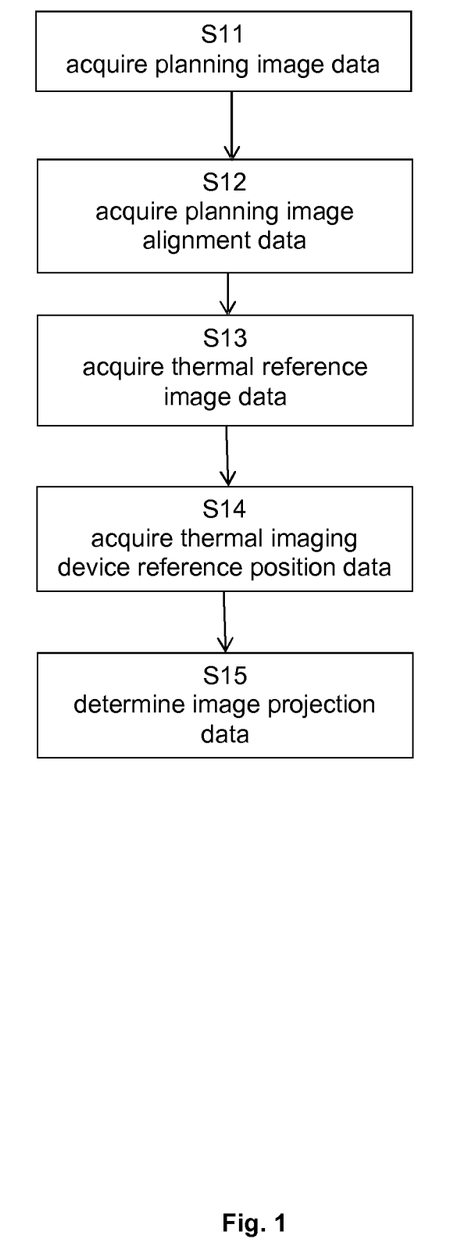
FIG. 1 is a flow diagram showing the basic steps of the disclosed method.

FIG. 1 is a flow diagram illustrating the basic steps of the disclosed method which in the illustrative example of FIG. 1 starts with a step S11 of acquiring the planning image data. In subsequent step S12, the planning image data is acquired, followed by step S13 which encompasses acquiring the thermal reference image data. Then, step S14 acquires the thermal imaging device reference position data. Steps S11 to S14 serve as input steps for the last step shown in FIG. 1 which is step S15 encompassing determination of the image projection data.

Figure 2:
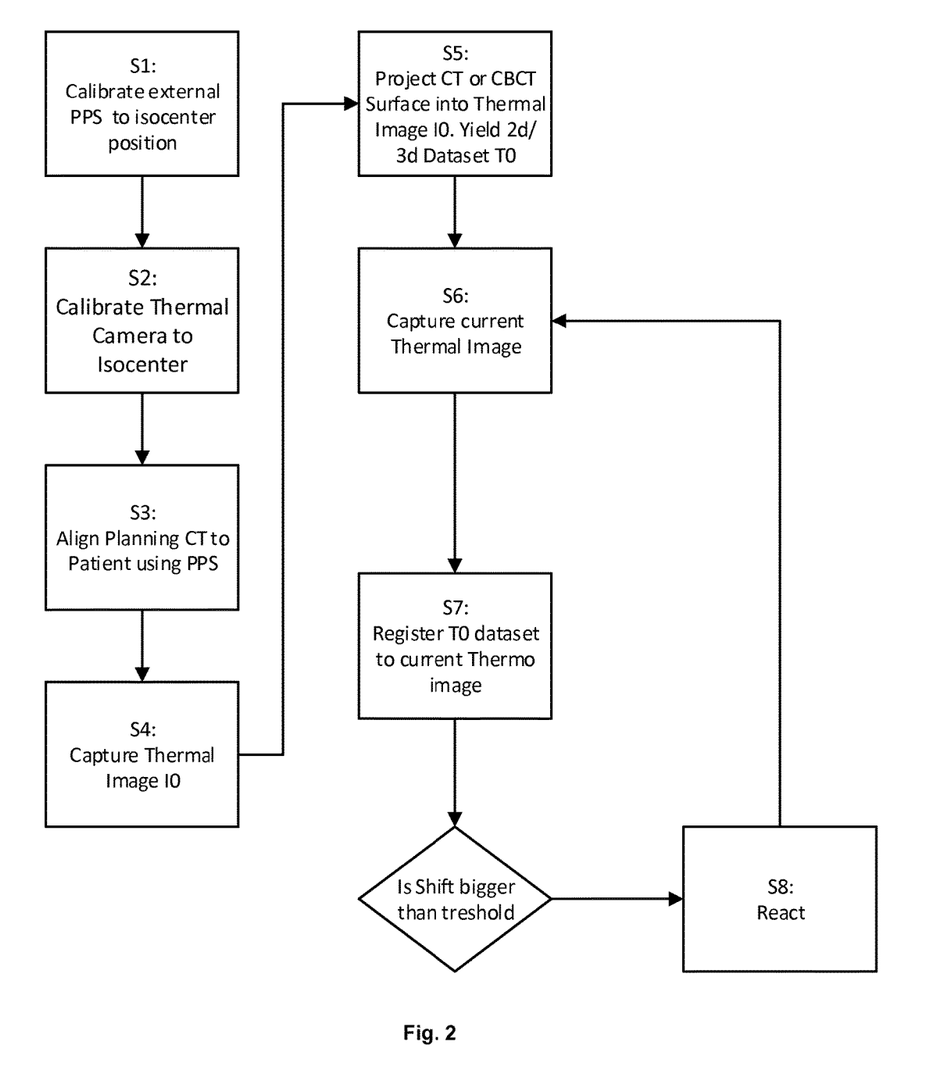
FIG. 2 is an embodiment of the flow diagram of FIG. 1.

FIG. 2 shows how the algorithm of FIG. 1 may serve as a basis for monitoring the patient's position using the thermal current image data. Step S2 corresponds to step S14 of FIG. 1, step S3 encompasses step S11 of FIG. 1, step S4 corresponds to step S13 of FIG. 1, and step S5 corresponds to step S15 of FIG. 1. PPS is an abbreviation for "patient positioning system". A PPS may be a Stereo-X-Ray or a CBCT, and may use portal image-based positioning or any other known accurate state-of-the-art CT-based positioning method.

Steps S1 and S2 encompass calibration of a PPS and a (thermal) camera to the same coordinate system. The first two steps have to be carried out pre-fractional (i.e. before therapy starts). Both systems have to be calibrated to the same coordinate system with the same origin (for example, in the isocentric coordinate system). For example a phantom can be placed on the couch and can be placed exactly in calibrated room lasers that define the isocentre. The phantom then exposes internal structures that are visible in X-Ray or CT so the PPS can register the phantom and save that coordinate system as reference point.

The same phantom can also be augmented with thermal markers like light-emitting diodes (LEDs) that are mounted at well-defined positions on the phantom. Using 2D-3D correspondences between the thermal markers as seen in the thermal camera and its corresponding relative 3D position as defined in the model of the phantom we can use e.g. the method as described in Kneip, L., Scaramuzza, D., Siegwart, R.: A Novel Parametrization of the Perspective-three-Point Problem for a Direct Computation of Absolute Camera Position and Orientation. In: Proc. of CVPR 2011, pp. 2969-2976 (2011) to solve the so called P-n-P problem and compute the pose of the camera with respect to an isocentric coordinate system denoted as [R|t], also called 'extrinsic camera parameters'.

For the system to work also the lense-distortion or 'intrinsic' camera parameters K of the camera must be known so that the following mathematical model of the camera can be built:

$$m_i = K[R|t]M_i \quad (1)$$

where $M_i$ is a point in 3-d space in homogeneous coordinates and $m_i$ the location of projection by $M_i$ onto the image plane of the thermal camera in 2d homogeneous coordinates. This can be done using a variant of Zhang, Z.: "A flexible new technique for camera calibration." Pattern Analysis and Machine Intelligence, IEEE Transactions on 22.11 (2000): pp. 1330-1334, where they minimize the re-projection error of a set of images of a known planar pattern that is varied in pose in front of the camera. This planar pattern can be generated using the same or a separate calibration phantom using LED images or other types of thermally visible markers.

Step S3 is directed to patient setup by the PPS. Before the treatment can begin, the patient has to be positioned using the PPS (e.g. using CBCT registration or stereoscopic X-Ray/CT registration). The effect of this step is that following steps S1 and S2, the position of the planning CT relative to the thermal/video camera is known.

Steps S4 and S5 are directed to taking the thermal reference image called thermal image I0 as a reference data set and matching it with (projecting it onto) the planning CT which embodies the planning image data. Using the camera model defined in S2, a set of corresponding 2d/3d points [M_i, m_i] is established by applying formula (1) to all visible surface points of the planning CT. Thus, a correspondence is received for each thermal pixel for which a corresponding point on the 3D surface exists. To extract the surface points of a CT, for example a "Marching Cubes" algorithm can be used like the one described in William E. Lorensen, Harvey E. Cline: Marching Cubes: A high resolution 3D surface construction algorithm. In: Computer Graphics, vol. 21, no. 4, July 1987, pp. 163-169.

Steps S6 and S7 are directed to monitoring the patient's position solving the perspective-n-point (PnP) problem. Having initialized the reference data set, new camera images are captured continuously and 2D-2D image registration (e.g. optical flow) between the reference thermal image I0 and the current thermal image can be applied. For each pixel location x in the reference 2D image I0 a 2D motion trail to the current thermal image is computed by minimizing $$\sum_x [I(W(x; p)) - T(x)]^2 \quad (2)$$

where W(x; p) translates a pixel x (or pixel neighbourhood in practice) according to a two-dimensional translation vector p, I(x) is the image function relating the "Intensity" (colour) value with the pixel position x, and T(x) is the template contained in the reference data set at the position of pixel x. This yields 2D pixel trajectories of the moving 3D (three-dimensional) scene. An applicable way to optimize this function is described in Bruce D. Lucas, Takeo Kanade "An iterative image registration technique with an application to stereo vision", Proceedings of the 7th International Joint Conference on Artificial Intelligence—volume 2, Vancouver, BC, Canada, pp. 674-679, 1981.

Figure 3:
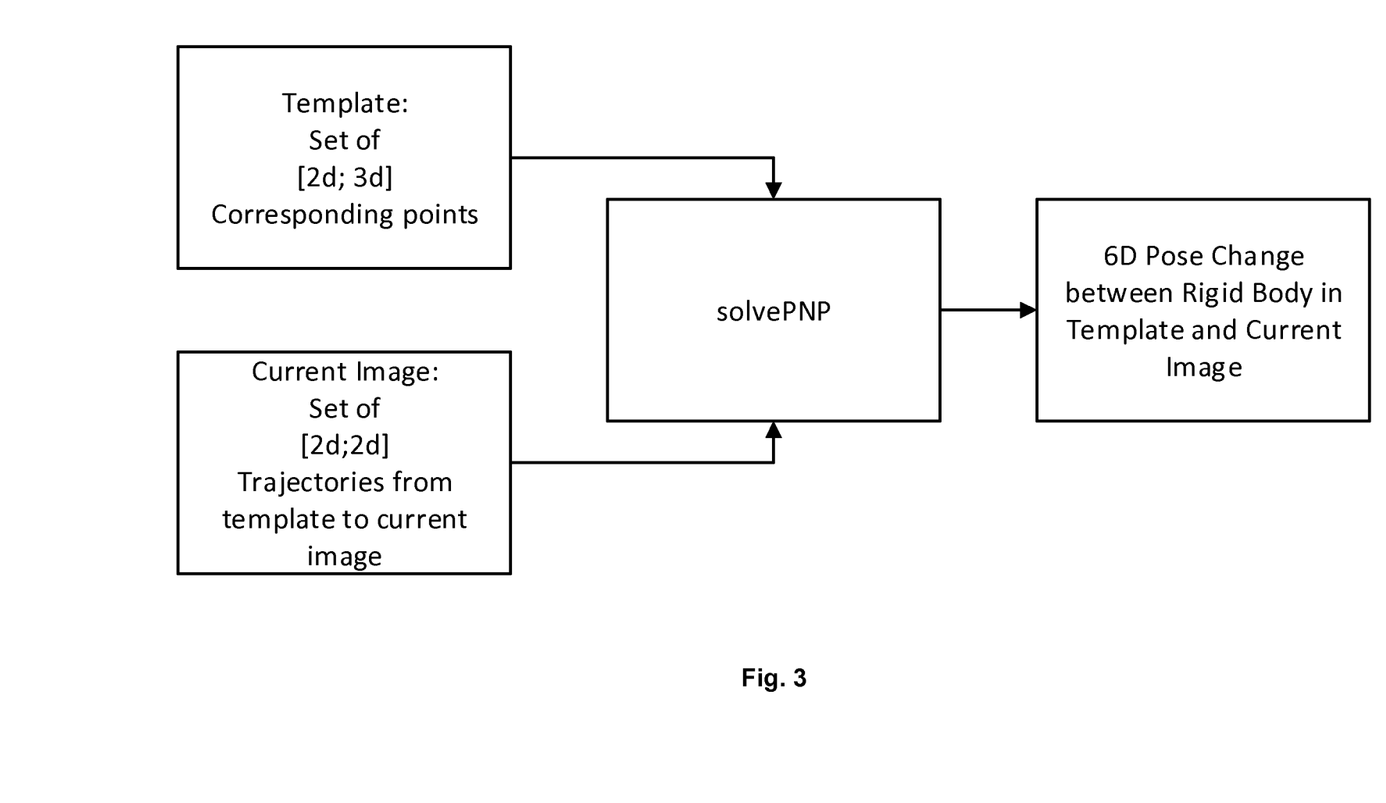
FIG. 3 shows an algorithm for determining the thermal position history data.

As shown in FIG. 3, using the 2D/3D dataset T0 and the 2D motion vectors between the pixels in the reference thermal image and the pixels in the current thermal image we can again solve the Perspective-n-Point-Problem and calculate the 6D (six-dimensional) pose change between the patient body in reference position and the patient body represented in the current image.

Figure 4:
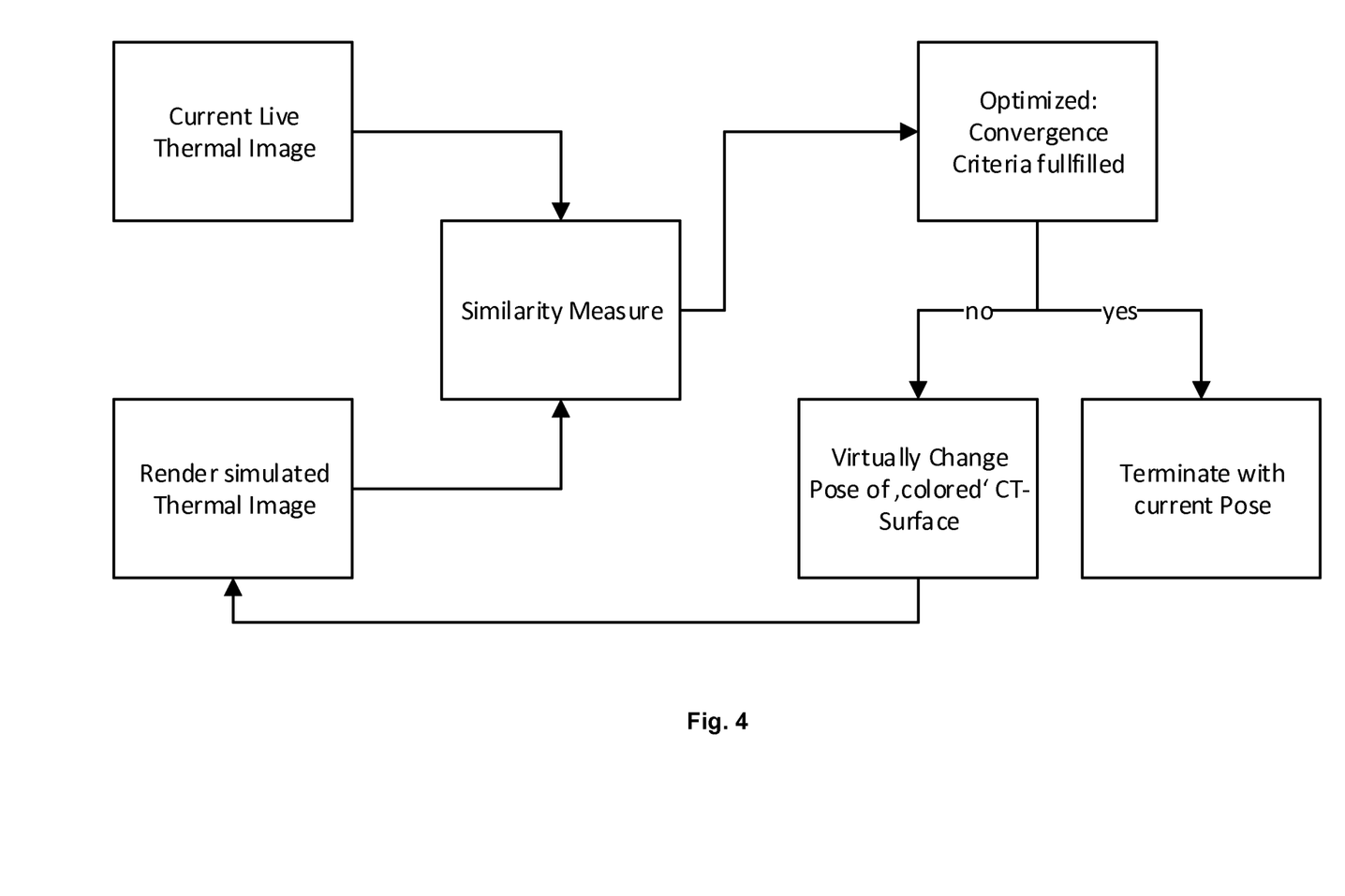
FIG. 4 shows an algorithm for conducting positional monitoring.

FIG. 4 illustrates that using the 2D/3D reference data set T0 it is possible to generate a 3D voxel dataset where each surface voxel is augmented using the colour information of the camera. This 3D voxel dataset can then be used to render 'virtual camera images' that mimic the appearance of the patient with respect to a certain pose. The pose 3D voxel data-set is varied and the 'virtual camera images' are compared with the real images until the difference between the two is minimal. The final pose is the result. A detailed description on this approach can be found in Crivellaro, A., Fua, P., & Lepetit, V. (2014). Dense Methods for Image Alignment with an Application to 3D Tracking. EPFL Report, pp. 1-25, section 7.2.

S8 relates to a possible reaction in dependence on the result of determining the pose change. In the context of radiation therapy the step could be moving the couch with the patient placed on it whenever the pose change between the reference measurement as depicted by the reference thermal image and the current measurement as depicted by the current thermal image exceeds a predefined threshold. As the approach of solving the pose change via solving the Perspective-N-Point problem is supposed to be very efficient, such a signal is most likely usable for live couch compensation or radiation therapy beam adaptation.

Figure 5:
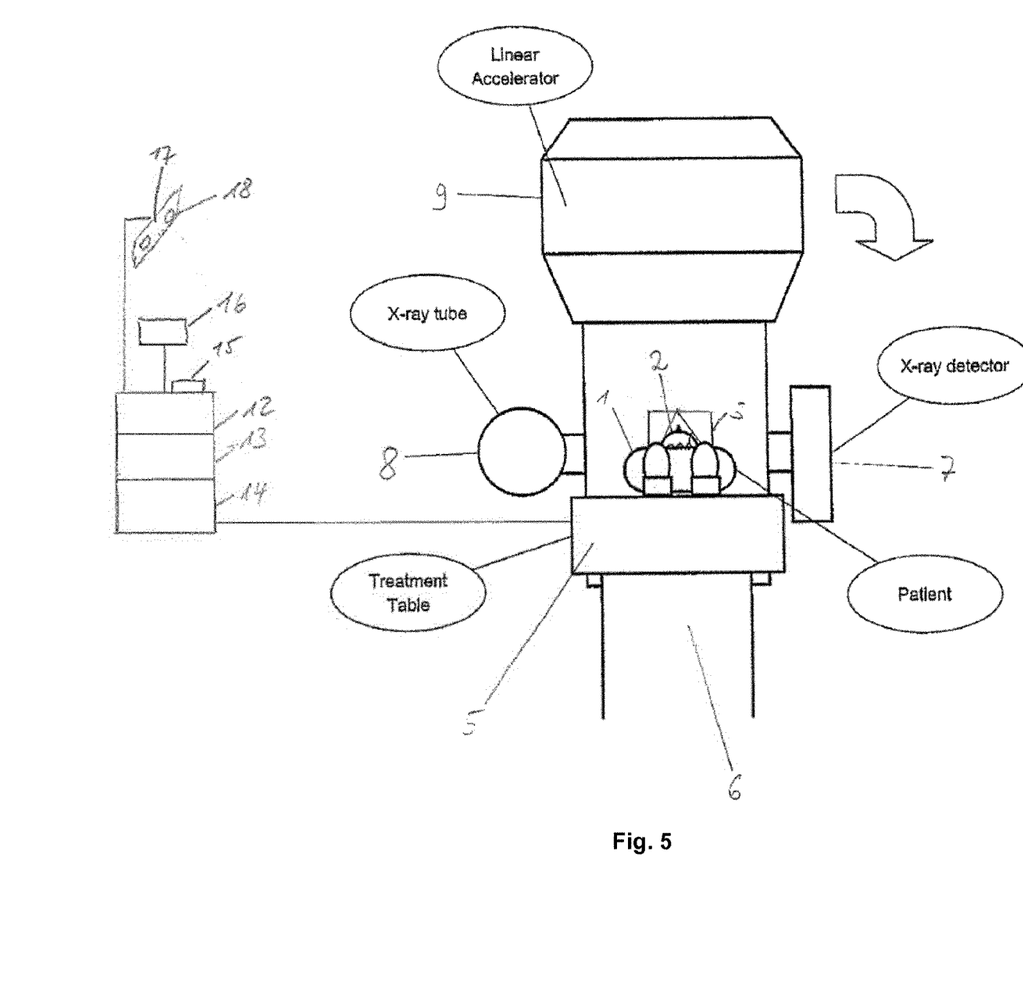
FIG. 5 illustrates the system for use with the disclosed method.

FIG. 5 shows a system for executing the method disclosed herein. The system comprises a computer having a processor 12 and a volatile memory (RAM) 13 which are operably coupled to a non-volatile memory 14 being an electronic data storage device (such as a hard disk) storing at least the planning image data, the reference structure position data and the imaging device position data. The computer is also coupled to an input device (such as at least one of a keyboard or a pointing device like a mouse) 15 and a display device 16 which can be embodied by a monitor. Furthermore, the computer is operably coupled to the thermal imaging device embodied by a thermal camera (an infrared-sensitive camera) 17 having two optical units 18 for taking the digital thermal image described by the thermal image data. The computer is also operably coupled to at least one of a treatment device 9 being a linear accelerator having a beam source for emitting an ionizing treatment beam which has a specifiable position relative to a patient support unit embodied by a couch 5 on which the patient's body 1 is positioned. A reference structure represented by an open face mask 3 may be attached to the patient's face 2. The treatment device further may comprise an x-ray tube 8 and an x-ray detector 7 for taking x-ray images for checking the patient's position during the treatment. The computer may alternatively or additionally be operably coupled to a motion control unit embodied by a motor 6 for driving the couch 5 (treatment table) to a desired position relative to the beam source.

The disclosed method achieves a 2D/3D registration between an optical (infrared) camera and a CT surface.

The disclosed method provides for the following novel and/or advantageous aspects:

1. A solution to the problem of registering a CT dataset to an optical camera for radiotherapy motion management is provided that can be used without any prior assumptions about room-lighting or the patient's skin tone.
2. A patient's subtle motion can be monitored without having to deal with the typical problems of the ICP (iterative closest point) algorithm and noisy and incomplete point clouds.
3. The setup is less complicated/cost efficient as one can use readily available video cameras or a thermal camera to track the patient's position without the need of an additional calibrated structured light projector.

The invention claimed is:

1. A computer-implemented method for treatment of a patient by at least one of radiotherapy or radiosurgery, the method comprising executing, on at least one processor of at least one computer, steps of:
   acquiring, by the at least one processor, planning image data describing a digital planning image of an anatomical body part of a body of the patient;
   acquiring, by the at least one processor, planning image alignment data describing a relative position between the anatomical body part and a predetermined reference position at the point in time when the planning image data was generated;
   acquiring, by the at least one processor, thermal reference image data describing a thermal reference image of the anatomical body part;
   acquiring, by the at least one processor, thermal imaging device reference position data describing a relative position between a thermal imaging device used for taking the thermal reference image and the predetermined reference position;
   determining, by the at least one processor and based on the planning image data and the planning image alignment data and the thermal reference image data and the thermal imaging device reference position data, image projection data describing a projection of the image representation of at least the anatomical body part described by the planning image data onto the image representation of the anatomical body part described by the thermal reference image data;
   determining treatment control data describing a command for controlling a treatment device usable for at least one of radiotherapy or radiosurgery based on the image projection data.

2. The method according to claim 1, comprising:
   determining, by the at least one processor and based on the thermal reference image data and the thermal imaging device reference position data, body part reference position data describing a relative position between the anatomical body part and the reference position at the point in time at which the thermal reference image was taken, wherein
   the image projection data is determined, by the at least one processor, based on the body part reference position data.

3. The method according to claim 1, comprising:
   acquiring, by the at least one processor, thermal current image data describing a thermal current image of the anatomical body part which has been taken after the thermal reference image was taken;
   determining, by the at least one processor and based on the thermal current image data and the thermal reference image data, thermal position history data describing a positional history of the anatomical body part described by a transformation between the position of the anatomical body part at the point in time at which the thermal reference image was taken and the position of the anatomical body at the point in time at which the thermal current image was taken.

4. The method according to claim 3, comprising:
   acquiring, by the at least one processor, thermal imaging device current position data describing a relative position between a thermal imaging device used for taking the thermal current image and the predetermined reference position;
   determining, by the at least one processor and based on the thermal current image data and the thermal imaging device current position data, body part current position data describing a relative position between the anatomical body part and the reference position at the point in time at which the thermal current image was taken, wherein
   the thermal position history data is determined, by the at least one processor, based on the body part current position data.

5. The method according to claim 4, wherein the thermal imaging device used for taking the thermal current image is identical to the thermal imaging device used for taking the thermal reference image.

6. The method according to claim 4, wherein the thermal imaging device current position data is identical to the thermal imaging device reference position data.

7. The method according to claim 3, comprising:
   determining, by the at least one processor and based on the thermal reference image data and the thermal current image data, thermal transformation data describing a transformation between the reference thermal image and the current thermal image;
   wherein the thermal position history data is determined, by the at least one processor, based on the thermal transformation data.

8. The method according to claim 3, comprising:
   determining, by the at least one processor and based on the thermal position history data, positional difference data describing a difference between a relative position between the position of the anatomical body part at the point in time at which the thermal reference image was taken and the position of the anatomical body at the point in time at which the thermal current image was taken.

9. The method according to claim 8, comprising:
acquiring, by the at least one processor, positional difference threshold data describing a threshold value of the difference between the position of the anatomical body part at the point in time at which the thermal reference image was taken and the position of the anatomical body at the point in time at which the thermal current image was taken;
determining, by the at least one processor and based on the positional difference data and the positional difference threshold data, the treatment control data describing the command for controlling the treatment device usable for the at least one of radiotherapy or radiosurgery.

10. The method according to claim 9, wherein the treatment control data is determined by comparing the difference between the relative position between the position of the anatomical body part at the point in time at which the thermal reference image was taken and the position of the anatomical body at the point in time at which the thermal current image was taken to the threshold value, wherein the treatment control data is determined if the comparison results in that the difference exceeds the threshold value.

11. The method according to claim 10, wherein the command for controlling the treatment device comprises at least one of
a command for controlling emission of a treatment beam by a beam source of the treatment device; or
a command for changing a relative position between the patient's body and the beam source by moving a patient support unit of the treatment device.

12. The method according to claim 1, wherein the predetermined reference position is the isocentre of a treatment device usable for treating the patient with at least one of radiotherapy or radiosurgery.

13. The method according to claim 1, wherein the planning image data has been generated by applying a tomographic imaging modality to the anatomical body part or by imaging the anatomical body part with an infrared-sensitive imaging device.

14. A non-transitory computer-readable medium comprising instructions that, in response to execution of the instructions by a computing system, cause the computing system to perform the following operations:
acquire, by at least one processor, planning image data describing a digital planning image of an anatomical body part of a body of a patient;
acquire, by the at least one processor, planning image alignment data describing a relative position between the anatomical body part and a predetermined reference position at the point in time when the planning image data was generated;
acquire, by the at least one processor, thermal reference image data describing a thermal reference image of the anatomical body part;
acquire, by the at least one processor, thermal imaging device reference position data describing a relative position between a thermal imaging device used for taking the thermal reference image and the predetermined reference position;
determine, by the at least one processor and based on the planning image data and the planning image alignment data and the thermal reference image data and the thermal imaging device reference position data, image projection data describing a projection of the image representation of at least the anatomical body part described by the planning image data onto the image representation of the anatomical body part described by the thermal reference image data.

15. A system for treatment of a patient by at least one of radiotherapy or radiosurgery, the system comprising:
at least one computer having at least one processor having associated memory, the memory having instructions that, in response to execution of the instructions by the at least one processor, causes the at least one computer having the at least one processor to:
acquire, by the at least one processor, planning image data describing a digital planning image of an anatomical body part of a body of a patient;
acquire, by the at least one processor, planning image alignment data describing a relative position between the anatomical body part and a predetermined reference position at the point in time when the planning image data was generated;
acquire, by the at least one processor, thermal reference image data describing a thermal reference image of the anatomical body part;
acquire, by the at least one processor, thermal imaging device reference position data describing a relative position between a thermal imaging device used for taking the thermal reference image and the predetermined reference position;
determine, by the at least one processor and based on the planning image data and the planning image alignment data and the thermal reference image data and the thermal imaging device reference position data, image projection data describing a projection of the image representation of at least the anatomical body part described by the planning image data onto the image representation of the anatomical body part described by the thermal reference image data;
determine treatment control data describing a command for controlling a treatment device usable for at least one of radiotherapy or radiosurgery based on the image projection data;
at least one electronic data storage device storing at least the planning image data, the planning image alignment data and thermal imaging device reference position data;
a thermal imaging device for taking the reference thermal image, the thermal imaging device being operably coupled to the at least one processor of the at least one computer for transmitting a signal to the at least one processor corresponding to the thermal reference image data;
the treatment device usable for treating the patient with at least one of radiotherapy or radiosurgery; and
a patient support unit for supporting the patient's body,
wherein the at least one processor of the at least one computer is operably coupled to the at least one electronic data storage device for acquiring, from the at least one data storage device, the planning image data, the planning image alignment data and thermal imaging device reference position data; and
wherein the at least one processor of the at least one computer is operably coupled to at least one of the treatment device or the patient support unit.

* * * * *